United States Patent
Hane et al.

(10) Patent No.: US 10,891,352 B1
(45) Date of Patent: Jan. 12, 2021

(54) CODE VECTOR EMBEDDINGS FOR SIMILARITY METRICS

(71) Applicant: Optum, Inc., Minnetonka, MN (US)

(72) Inventors: Christopher A. Hane, Eden Prairie, MN (US); Alexander Kravetz, Cambridge, MA (US)

(73) Assignee: Optum, Inc., Minnetonka, MN (US)

( * ) Notice: Subject to any disclaimer, the term of this patent is extended or adjusted under 35 U.S.C. 154(b) by 371 days.

(21) Appl. No.: 15/927,188

(22) Filed: Mar. 21, 2018

(51) Int. Cl.
*G06F 17/16* (2006.01)
*G06K 9/62* (2006.01)
*G16H 10/60* (2018.01)
*G06N 20/00* (2019.01)
*G06F 40/157* (2020.01)

(52) U.S. Cl.
CPC ............ *G06F 17/16* (2013.01); *G06F 40/157* (2020.01); *G06K 9/6215* (2013.01); *G06N 20/00* (2019.01); *G16H 10/60* (2018.01)

(58) Field of Classification Search
CPC ....... G06F 17/16; G06F 40/157; G06N 20/00; G06K 9/6215; G16H 10/60
See application file for complete search history.

(56) References Cited

U.S. PATENT DOCUMENTS

| | | |
|---|---|---|
| 6,266,645 B1 | 7/2001 | Simpson |
| 6,556,977 B1 * | 4/2003 | Lapointe ................ G16H 50/20 706/15 |
| 6,915,254 B1 | 7/2005 | Heinze et al. |
| 7,499,048 B2 | 3/2009 | Sieracki et al. |

(Continued)

FOREIGN PATENT DOCUMENTS

WO 2014/201515 A1 12/2014

OTHER PUBLICATIONS

Pakhomov, S., et al., Automating the Assignment of Diagnosis Codes to Patient Encounters Using Example-based and Machine Learning Techniques, Sep. 1, 2006, Journal of the American Medical Informatics Association, 516-525, 13/5, https://watermark.silverchair.com/13-5-516.pdf?token=AQECAHi208BE49Ooan9kkhW_Ercy7Dm3ZL_9Cf3qfKAc485ys . . . .

(Continued)

*Primary Examiner* — Xuemei G Chen
(74) *Attorney, Agent, or Firm* — Alston & Bird LLP (57) ABSTRACT

Aggregate vectors corresponding to non-textual information/data are provided in a multi-dimensional space. A computing entity access a plurality of instances of medical information comprising medical codes. The computing entity generates one or more medical sentences from the plurality of instances of medical information. Each medical sentence comprises one or more medical codes. The computing entity generates an embedding vector dictionary comprising a plurality of multi-dimensional vectors based on a medical embedding model trained using machine learning and the one or more medical sentences. Each multi-dimensional vector corresponds to a medical code. The computing entity generates a plurality of aggregate vectors based on the embedding vector dictionary and analyzes at least a portion of the plurality of aggregate vectors to identify two or more aggregate vectors that are similar or different based on a distance between the two or more aggregate vectors in the multi-dimensional space.

20 Claims, 6 Drawing Sheets

(56) References Cited

U.S. PATENT DOCUMENTS

| | | | |
|---|---|---|---|
| 7,801,839 B2* | 9/2010 | Kates | G16H 50/20 706/21 |
| 8,255,412 B2* | 8/2012 | Gao | G06F 16/24578 707/765 |
| 8,296,247 B2 | 10/2012 | Zhang et al. | |
| 8,320,651 B2 | 11/2012 | Vining et al. | |
| 8,504,392 B2 | 8/2013 | Saria et al. | |
| 8,856,156 B1 | 10/2014 | McNair et al. | |
| 8,963,914 B2 | 2/2015 | Rawat et al. | |
| 9,805,160 B2* | 10/2017 | Morris | G16H 10/60 |
| 9,828,671 B2 | 11/2017 | Shibusawa et al. | |
| 10,176,645 B2 | 1/2019 | Canfield et al. | |
| 2005/0240439 A1 | 10/2005 | Covit et al. | |
| 2008/0288292 A1* | 11/2008 | Bi | G16H 10/60 705/3 |
| 2012/0033871 A1 | 2/2012 | Vining et al. | |
| 2012/0166212 A1 | 6/2012 | Campbell | |
| 2012/0185275 A1 | 7/2012 | Loghmani | |
| 2013/0080187 A1 | 3/2013 | Bacon et al. | |
| 2014/0249849 A1 | 9/2014 | Khare et al. | |
| 2014/0278490 A1 | 9/2014 | Namazifar et al. | |
| 2015/0095016 A1 | 4/2015 | Karres et al. | |
| 2015/0356198 A1 | 12/2015 | D et al. | |
| 2016/0012202 A1 | 1/2016 | Hu et al. | |
| 2016/0063214 A1* | 3/2016 | Blue | G16H 50/70 705/3 |
| 2016/0092641 A1 | 3/2016 | Delaney et al. | |
| 2017/0132288 A1* | 5/2017 | Ho | G06F 40/30 |
| 2017/0161619 A1* | 6/2017 | Franceschini | G06N 5/022 |
| 2017/0308981 A1 | 10/2017 | Razavian et al. | |
| 2018/0025121 A1* | 1/2018 | Fei | G16H 10/60 705/3 |
| 2018/0089382 A1* | 3/2018 | Allen | G16H 50/70 |
| 2018/0089383 A1* | 3/2018 | Allen | G16H 15/00 |
| 2018/0165418 A1* | 6/2018 | Swartz | G16H 50/30 |
| 2018/0260381 A1* | 9/2018 | Carreras | G06F 40/211 |
| 2018/0293499 A1* | 10/2018 | He | G06F 40/216 |
| 2018/0315440 A1* | 11/2018 | Inaba | G06F 40/40 |
| 2019/0005019 A1* | 1/2019 | Burke | G06F 19/36 |
| 2019/0096140 A1 | 3/2019 | Canfield et al. | |
| 2019/0114318 A1* | 4/2019 | Zhou | G06N 5/022 |
| 2019/0171792 A1* | 6/2019 | Manica | G06F 40/20 |
| 2019/0188271 A1* | 6/2019 | Murdock | G06F 16/24578 |
| 2019/0188848 A1* | 6/2019 | Madani | A61B 6/5229 |
| 2019/0220694 A1* | 7/2019 | Biswas | G06K 9/468 |
| 2019/0236206 A1* | 8/2019 | Chowdhury | G06F 16/335 |
| 2019/0251084 A1* | 8/2019 | Wang | G16H 10/60 |
| 2019/0286759 A1* | 9/2019 | Wilkins | G06F 30/00 |
| 2020/0034366 A1* | 1/2020 | Kivatinos | G06K 9/6276 |
| 2020/0251219 A1* | 8/2020 | Fukunishi | G16H 70/40 |

OTHER PUBLICATIONS

Okamoto, K., et al., Automatic DPC code selection from discharge summaries using several machine learning methods, Dec. 1, 2011, Transactions of Japanese Society for Medical and Biological Engineering, 40-47, 49/1, https://www.jstage.jst.go.jp/article/jsmbe/49/1/49_1_40/_pdf/-char/ja, Aug. 14, 2018 (Japanese Article—English Abstract only).

Lingren, T., et al., Electronic Health Record Based Algorithm to Identify Patients with Autism Spectrum Disorder, Jul. 29, 2016, Plos One, 1-16, http://nrs.harvard.edu/urn-3:HUL.InstRepos:29002605, Aug. 14, 2018.

Jara, J. L., et al., Empirical evaluation of three machine learning method for automatic classification of neoplastic diagnoses/ Evaluación empírica de tres métodos de aprendizaje automático para clasificar automáticamente diagnósticos de neoplasias, Dec. 1, 2011, Ingeniare. Revista chilena de ingeniería, 359-368, 19/3, https://scielo.conicyt.cl/pdf/ingeniare/v19n3/art06.pdf, Aug. 14, 2018.

Feng, Yujuan et al. "Patient Outcome Prediction Via Convolutional Neural Networks Based on Multi-Granularity Medical Concept Embedding," 2017 IEEE International Converence on Bioinformatics and Biomedicine (BIBM), Nov. 13, 2017, pp. 770-777.

International Searching Authority, International Search Report and Written Opinion for International Application No. PCT/US2019/041784, Nov. 27, 2019, (18 pages), European Patent Office, Rijswijk, The Netherlands.

Wang et al., "Diagnosis Code Assignment Using Sparsity-Based Disease Correlation Embedding," Journal of Latex Class Files, vol. 13, No. 9, Sep. 2014, pp. 1-13.

Shubham Agarwal, Word to Vectors—Natural Language Processing, May 18, 2017, https://towardsdatascience.com/word-to-vectors-natural-language-processing-b253dd0b0817, Apr. 17, 2019.

Gonzenbach, "Sentiment Classification and Medical Health Record Analysis Using Convolutional Neural Networks," Swiss Federal Institute of Technology Zurich, May 24, 2016, pp. 1-56.

Bui Alex A.T. et al. "Medical Data Visualization: Toward Integrated Clinical Workstations," InMedical Imaging Informatics, (2010), pp. 139-193. Springer, Boston, MA. DOI: 10.1007/978-1-4419-0385-3_4.

Diseases of the Respiratory System: (ICD-10-CM Chapter 10, Codes J00-J99), General Surgery, Basicmedical Key, Jun. 3, 2017. [Retrieved from the Internet Feb. 23, 2020] <URL:https://basicmedicalkey.com/diseases-of-the-respiratory-system-icd-10-cm-chapter-10-codes-j00-j99/>.

Shi, Liehang et al. "Three-Dimensional Visual Patient Based on Electronic Medical Diagnostic Records," IEEE Journal of Biomedical and Health Informatics, vol. 22, No. 1, Jan. 2018, pp. 161-172.

* cited by examiner

CODE VECTOR EMBEDDINGS FOR SIMILARITY METRICS

FIELD

Various embodiments relate generally to generating and/or using code vector embeddings for use as and/or with a similarity metric. For example, an example embodiment provides generates medical code vector embeddings for use as a similarity measure.

BACKGROUND

Medical information is often encoded using medical codes such as diagnoses codes, procedure codes, prescription or drug codes, equipment codes, revenue codes, place of service codes, and/or the like. These medical codes are non-interpretable, alpha-numeric strings that can be quite specific. For example, a fracture of the left forearm may have a specific code that is different from the code for a fracture of the right forearm. However, in terms of the procedures and prescriptions provided to a patient, a right forearm fracture and a left forearm fracture are quite similar. Thus, human medical knowledge is generally required for determining the actual similar of a set of medical codes.

BRIEF SUMMARY

Various embodiments provide methods, apparatuses, computer program products, systems, and/or the like that provide aggregate vectors within a multi-dimensional space. In various embodiments, medical information/data is accessed and medical sentences are formed therefrom. In various embodiments, the medical sentences consist of one or more medical codes (e.g., diagnosis codes, procedure codes, prescription or drug codes, equipment codes, revenue codes, place of service codes, and/or the like). The medical sentences are then used to train a medical embedding model. For example, the medical embedding model may be trained using machine learning and a training data set comprising at least some of the medical sentences. The medical embedding model may then generate an embedding vector dictionary that links one or more medical codes of a medical code set to a multi-dimensional vector. Aggregate vectors corresponding to a patient, a particular patient visit, a provider, a provider group, a geographical area, a claim, and/or the like may be formed by aggregating the multi-dimensional vectors corresponding to an investigation set of medical codes corresponding to the patient, particular patient visit, provider, provider group, geographical area, claim or the like. In various embodiments, the multi-dimensional vectors corresponding to the investigation set of medical codes may be aggregated by adding or summing the multi-dimensional vectors corresponding to the investigation set, averaging the multi-dimensional vectors corresponding to the investigation set, finding or determining an angle separating the multi-dimensional vectors corresponding to the investigation set, or performing another vector function of the multi-dimensional vectors corresponding to the investigation set to form an aggregate vector corresponding to the patient, particular patient visit, provider, provider group, geographical area, claim or the like.

According to one aspect of the present invention, a method for providing aggregate vectors in a multi-dimensional space. In an example embodiment, the method comprises accessing, by a computing entity, a plurality of instances of medical information encoded using medical codes. The computing entity comprises a processor and a memory storing computer program code. The method further comprises generating, by the computing entity, one or more medical sentences from the plurality of instances of medical information. Each medical sentence comprises one or more medical codes. The method further comprises generating, by the computing entity, an embedding vector dictionary comprising a plurality of multi-dimensional vectors based on a medical embedding model trained using machine learning and the one or more medical sentences. The multi-dimensional vectors are in a multi-dimensional space having a configurable dimensionality. Each multi-dimensional vector corresponds to a medical code. The method further comprises generating, by the computing entity, a plurality of aggregate vectors based on the embedding vector dictionary; and analyzing, by the computing entity, at least a portion of the plurality of aggregate vectors to identify two or more aggregate vectors that are similar or different based on a distance or angle between the two or more aggregate vectors in the multi-dimensional space. The method may further comprise providing, by the computing entity, an output comprising the identified two or more aggregate vectors.

According to another aspect of the present invention, an apparatus is provided. In an example embodiment, the apparatus comprises at least one processor and at least one memory including computer program code for one or more programs. The at least one memory and the computer program code are configured to, with the at least one processor, cause the apparatus to at least access a plurality of instances of medical information encoded using medical codes; and generate one or more medical sentences from the plurality of instances of medical information. Each medical sentence comprises one or more medical codes. The at least one memory and the computer program code are further configured to, with the at least one processor, cause the apparatus to at least generate an embedding vector dictionary comprising a plurality of multi-dimensional vectors based on a medical embedding model trained using machine learning and the one or more medical sentences. The multi-dimensional vectors are in a multi-dimensional space having a configurable dimensionality. Each multi-dimensional vector corresponds to a medical code. The at least one memory and the computer program code are further configured to, with the at least one processor, cause the apparatus to at least generate a plurality of aggregate vectors based on the embedding vector dictionary; analyze at least a portion of the plurality of aggregate vectors to identify two or more aggregate vectors that are similar or different based on a distance or angle between the two or more aggregate vectors in the multi-dimensional space; and provide an output comprising the identified two or more aggregate vectors.

According to yet another embodiment, a computer program product is provided. In an example embodiment, the computer program product comprises at least one non-transitory computer-readable storage medium having computer-executable program code portions stored therein. The computer-executable program code portions comprise program code instructions. The computer program code instructions, when executed by a processor of a computing entity, are configured to cause the computing entity to at least access a plurality of instances of medical information encoded using medical codes; and generate one or more medical sentences from the plurality of instances of medical information. Each medical sentence comprising one or more medical codes. The computer program code instructions, when executed by a processor of a computing entity, are further configured to cause the computing entity to at least generate an embedding vector dictionary comprising a plurality of multi-dimensional vectors based on a medical embedding model trained using machine learning and the one or more medical sentences. The multi-dimensional vectors are in a multi-dimensional space having a configurable dimensionality. Each multi-dimensional vector corresponding to a medical code. The computer program code instructions, when executed by a processor of a computing entity, are further configured to cause the computing entity to at least generate a plurality of aggregate vectors based on the embedding vector dictionary; analyze at least a portion of the plurality of aggregate vectors to identify two or more aggregate vectors that are similar or different based on a distance or angle between the two or more aggregate vectors in the multi-dimensional space; and provide an output comprising the identified two or more aggregate vectors.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF SOME EXAMPLE EMBODIMENTS

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" (also designated as "/") is used herein in both the alternative and conjunctive sense, unless otherwise indicated. The terms "illustrative" and "exemplary" are used to be examples with no indication of quality level. Like numbers refer to like elements throughout.

I. General Overview

In various embodiments, methods, systems, apparatuses, computer program products, and/or the like are provided for providing aggregate vectors for one or more subjects in a multi-dimensional space. In various embodiments, the one or more subjects may each be a patient, a particular patient visit to a provider, a provider, a provider group, a geographical area, a medical insurance claim, and/or the like. Various embodiments further comprise use of the aggregate vectors for performing one or more similarity or difference determinations for the corresponding subjects. For example, the distance between two aggregate vectors may provide a similarity metric indicating how similar or how different the corresponding two subjects are. In another example, the angle between two aggregate vectors may provide a similarity metric indicating how similar or how different the corresponding two subjects are. For example, in an example embodiment, the aggregate vectors corresponding to two or more claims may be used to identify a first claim that was resubmitted as a second, different claim (e.g., due to the first claim being denied) and to link the first and second claims. In another example, the aggregate vectors corresponding to a plurality of providers may be used to identify providers that have similar practices. In various embodiments, a provider is a healthcare provider such as a doctor, physician, surgeon, dentist, optometrist, medical specialist, physician assistant, registered nurse, nurse practitioner, and/or other healthcare provider, or collection of these entities acting as a group, practice, or hospital.

In various embodiments, aggregate vectors are generated based on an embedding vector dictionary. In an example embodiment, the embedding vector dictionary provides a multi-dimensional vector corresponding to each of one or more medical codes (e.g., procedure codes, diagnosis codes, prescription or drug codes, equipment codes, revenue codes, place of service codes, and/or the like). In an example embodiment, the embedding vector dictionary is generated by accessing medical information/data, generating medical sentences comprising and/or consisting of medical codes based on the medical information/data, and training a medical embedding model using machine learning and a training data set comprising at least some of the medical sentences. The medical embedding model may in turn be used to generate the embedding vector dictionary.

II. Computer Program Products, Methods, and Computing Entities

Embodiments of the present invention may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of a data structure, apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

III. Exemplary System Architecture

Figure 1:
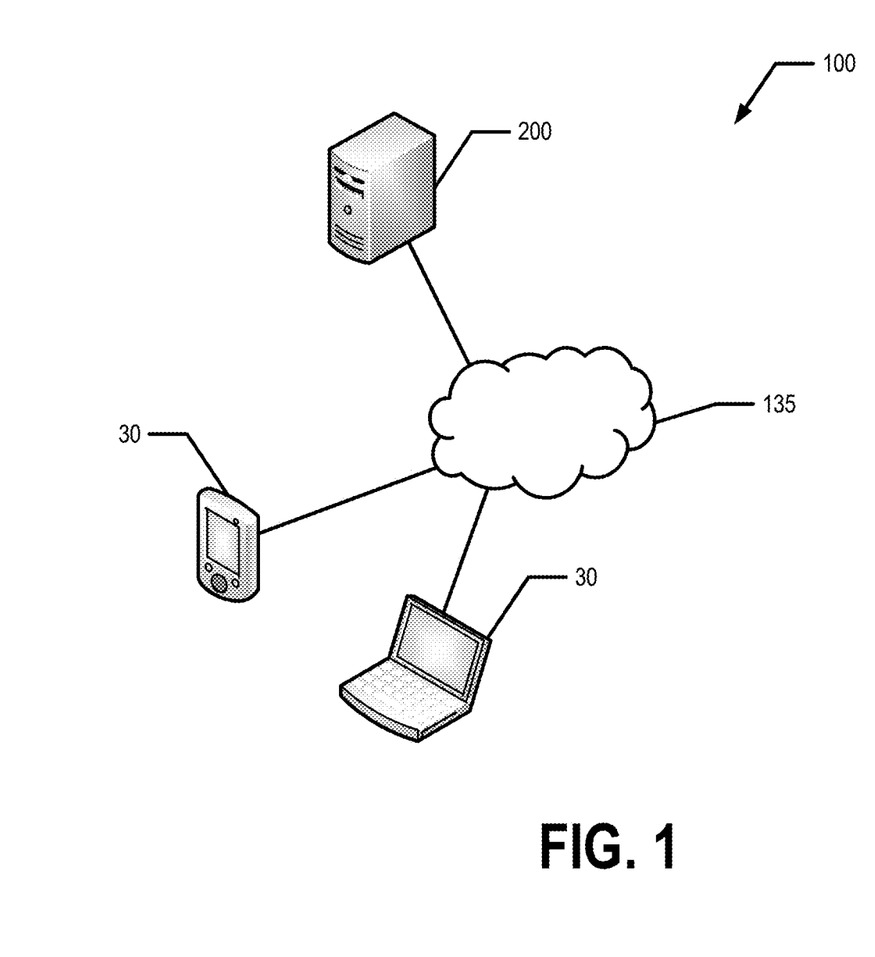
FIG. 1 is a diagram of a system that can be used to practice various embodiments of the present invention.

FIG. 1 provides an illustration of a system 100 that can be used in conjunction with various embodiments of the present invention. As shown in FIG. 1, the system 100 may comprise one or more computing entities 200, one or more user computing entities 30, one or more networks 135, and/or the like. Each of the components of the system may be in electronic communication with, for example, one another over the same or different wireless or wired networks 135 including, for example, a wired or wireless Personal Area Network (PAN), Local Area Network (LAN), Metropolitan Area Network (MAN), Wide Area Network (WAN), and/or the like. Additionally, while FIG. 1 illustrate certain system entities as separate, standalone entities, the various embodiments are not limited to this particular architecture.

a. Exemplary Computing Entity

Figure 2:
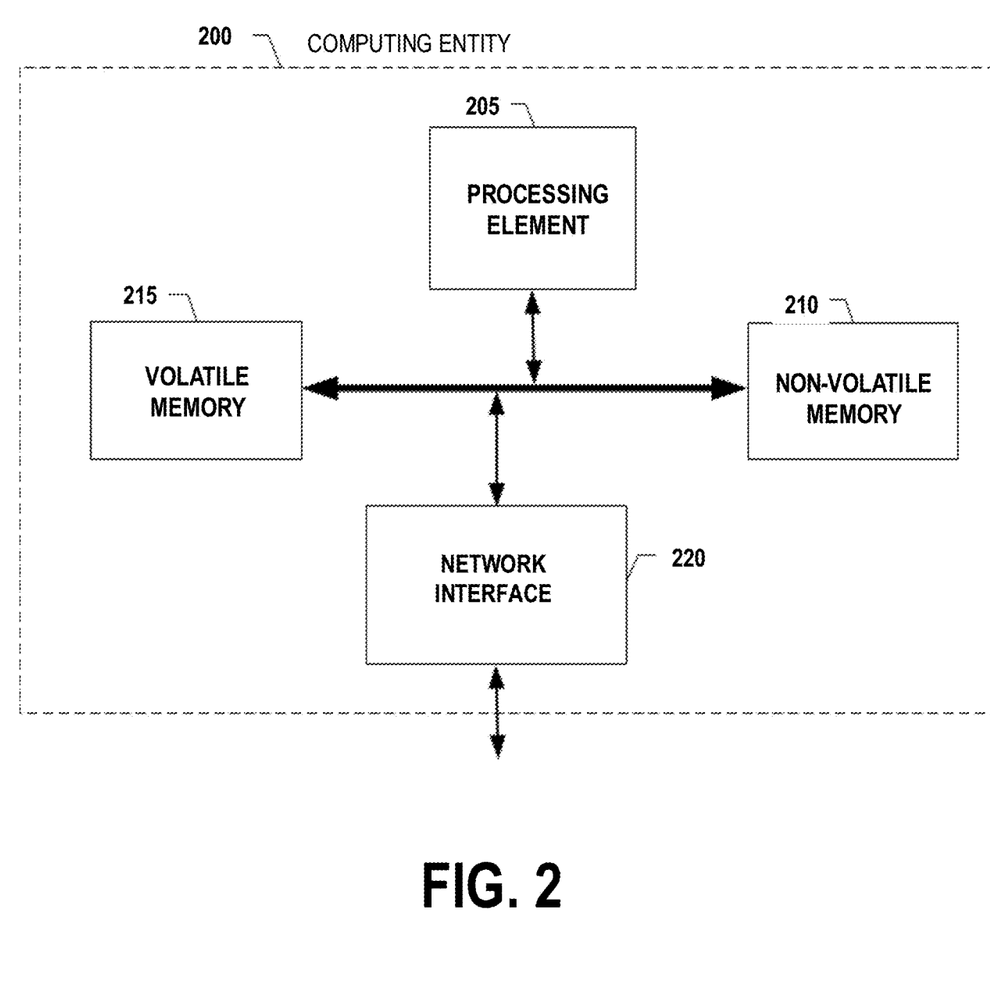
FIG. 2 is a schematic of a computing entity in accordance with certain embodiments of the present invention.

FIG. 2 provides a schematic of a computing entity 200 according to one embodiment of the present invention. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the computing entity 200 may also include one or more network and/or communications interfaces 220 for communicating with various computing entities, such as by communicating data, content, information, and/or similar terms used herein interchangeably that can be transmitted, received, operated on, processed, displayed, stored, and/or the like. For instance, the computing entity 200 may communicate with other computing entities 200, one or more user computing entities 30, and/or the like.

As shown in FIG. 2, in one embodiment, the computing entity 200 may include or be in communication with one or more processing elements 205 (also referred to as processors, processing circuitry, and/or similar terms used herein interchangeably) that communicate with other elements within the computing entity 200 via a bus, for example. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the computing entity 200 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably may refer to a structured collection of records or information/data that is stored in a computer-readable storage medium, such as via a relational database, hierarchical database, and/or network database.

In one embodiment, the computing entity 200 may further include or be in communication with volatile media (also referred to as volatile storage, memory, memory storage, memory circuitry and/or similar terms used herein interchangeably). In one embodiment, the volatile storage or memory may also include one or more volatile storage or memory media 315 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 305. Thus, the databases, database instances, database management system entities, data, applications, programs, program modules, scripts, source code, object code, byte code, compiled code, interpreted code, machine code, executable instructions, and/or the like may be used to control certain aspects of the operation of the computing entity 200 with the assistance of the processing element 205 and operating system.

As indicated, in one embodiment, the computing entity 200 may also include one or more network and/or communications interfaces 220 for communicating with various computing entities, such as by communicating data, content, information, and/or similar terms used herein interchangeably that can be transmitted, received, operated on, processed, displayed, stored, and/or the like. For instance, the computing entity 200 may communicate with computing entities or communication interfaces of other computing entities 200, user computing entities 30, and/or the like.

As indicated, in one embodiment, the computing entity 200 may also include one or more network and/or communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the computing entity 200 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra wideband (UWB), infrared (IR) protocols, near field communication (NFC) protocols, Wibree, Bluetooth protocols, wireless universal serial bus (USB) protocols, and/or any other wireless protocol. The computing entity 200 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the computing entity's 200 components may be located remotely from other computing entity 200 components, such as in a distributed system. Furthermore, one or more of the components may be aggregated and additional components performing functions described herein may be included in the computing entity 200. Thus, the computing entity 200 can be adapted to accommodate a variety of needs and circumstances.

b. Exemplary User Computing Entity

Figure 3:
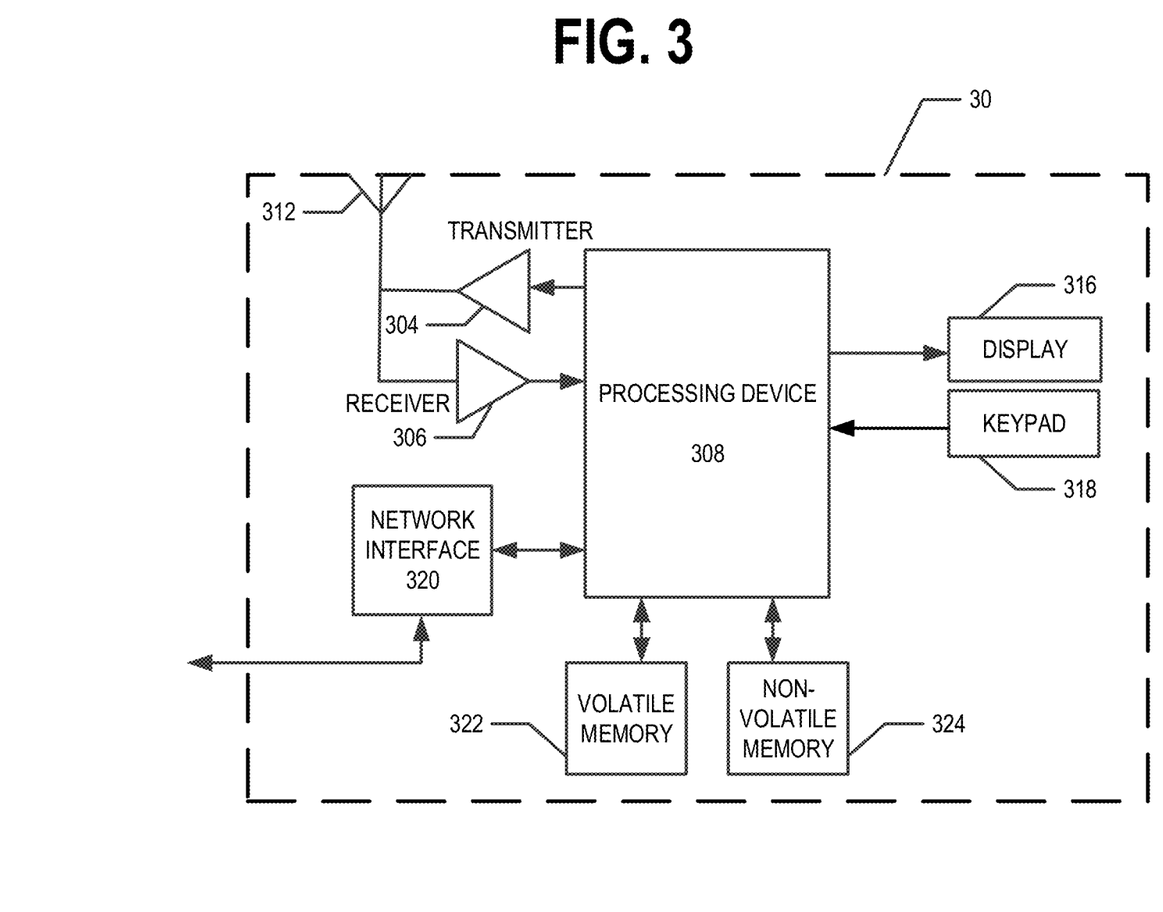
FIG. 3 is a schematic of a user computing entity in accordance with certain embodiments of the present invention.

FIG. 3 provides an illustrative schematic representative of user computing entity 30 that can be used in conjunction with embodiments of the present invention. As shown in FIG. 3, a user computing entity 30 can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various entities, such as a computing entity 200, another user computing entity 30, and/or the like. In this regard, the user computing entity 30 may be capable of operating with one or more air interface standards, communication protocols, modulation types, and access types. More particularly, the user computing entity 30 may operate in accordance with any of a number of wireless communication standards and protocols. In a particular embodiment, the user computing device 30 may operate in accordance with multiple wireless communication standards and protocols, such as GPRS, UMTS, CDMA2000, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 30 can communicate with various other entities using concepts such as Unstructured Supplementary Service information/data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 30 can also download changes, add-ons, and updates, for instance, to its firmware, software (e.g., including executable instructions, applications, program modules), and operating system.

According to one embodiment, the user computing entity 30 may include location determining aspects, devices, modules, functionalities, and/or similar words used herein interchangeably. For example, the user computing entity 30 may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data may be determined by triangulating the computing entity's 200' position in connection with a variety of other systems, including cellular towers, Wi-Fi access points, and/or the like. Similarly, the user computing entity 30 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing devices (e.g., smartphones, laptops) and/or the like. For instance, such technologies may include iBeacons, Gimbal proximity beacons, BLE transmitters, Near Field Communication (NFC) transmitters, and/or the like. These indoor positioning aspects can be used in a variety of settings to determine the location of someone or something to within inches or centimeters.

The user computing entity 30 may also comprise a user interface device comprising one or more user input/output interfaces (e.g., a display 316 and/or speaker/speaker driver coupled to a processing element 308 and a touch screen, keyboard, mouse, and/or microphone coupled to a processing element 308). For example, the user output interface may be configured to provide an application, browser, user interface, dashboard, webpage, and/or similar words used herein interchangeably executing on and/or accessible via the user computing entity 30 to cause display or audible presentation of information/data and for user interaction therewith via one or more user input interfaces. The user input interface can comprise any of a number of devices allowing the user computing entity 30 to receive data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 30 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 30 can collect information/data, user interaction/input, and/or the like.

The user computing entity 30 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the user computing entity 30.

c. Exemplary Networks

In one embodiment, any two or more of the illustrative components of the architecture of FIG. 1 may be configured to communicate with one another via respective communicative couplings to one or more networks 135. The networks 135 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 135 may have any suitable communication range associated therewith and may include, for example, global networks (e.g., the Internet), MANs, WANs, LANs, or PANs. In addition, the networks 135 may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms provided by network providers or other entities.

IV. Exemplary System Operation

Medical information/data (and similar words used herein interchangeably) is often encoded using medical codes. For example, procedure codes, diagnostic codes, prescription or drug codes, equipment codes, revenue codes, place of service codes, and/or the like may be used to encode various portions of an instance of medical information/data. The encoding of the medical information/data using medical codes is manually performed by a trained professional. For example, various colleges and universities offer certificate programs that train people to perform the encoding of the medical information/data into medical codes. Given the medical knowledge required to make sense of medical information/data encoded using medical codes, automated and/or computerized analysis of encoded medical information/data generally fails to capture the complexity and/or full picture provided by the encoded medical information/data. Moreover, computer analysis of medical information/data encoded in medical codes cannot be effectively performed using the same methodology of analyzing textual information. For example, grammar rules may be used to aid the analysis of textual information, but medical codes are not subject to any such grammar rules.

Various embodiments of the present invention provide a technical solution to these technical problems by transforming medical codes into multi-dimensional vectors in a multi-dimensional space. For example, a medical embedding model may be trained using machine learning such that the medical embedding model may generate an embedding vector dictionary. The embedding vector dictionary may link one or more medical codes to corresponding multi-dimensional vectors. The multi-dimensional vectors may be generated such that a first medical code and a second medical code that are closely related may be assigned and/or may correspond to multi-dimensional vectors that have a smaller distance or smaller angle therebetween in the multi-dimensional space than a third medical code and a fourth medical code that are not closely related. For example, current procedural terminology (CPT) code J9002, corresponding to doxorubicin administration, may correspond to a multi-dimensional vector that is closer to the multi-dimensional vector corresponding to diagnosis code C50.919, corresponding to breast cancer, than to the multi-dimensional vector corresponding to CPT code J0133, corresponding to injectable acyclovir. As should be understood, in this context, the term "closer" refers to a shorter distance or a smaller angle between the multi-dimensional vectors. Thus, the medical knowledge regarding the relationships between various codes may be encoded through the correspondence of medical codes with multi-dimensional vectors, as in the embedding vector dictionary.

In various embodiments, the embedding vector dictionary may be used to generate aggregate vectors that encode one or more instances of medical information/data. For example, a claim may be converted to an aggregate vector by aggregating the multi-dimensional vectors corresponding to each medical code of the claim. The aggregating of the multi-dimensional vectors may comprise adding the multi-dimensional vectors, averaging the multi-dimensional vectors, performing a weight average of the multi-dimensional vectors, and/or performing another vector operation on the multi-dimensional vectors. Aggregate vectors representing subjects (e.g., patients, particular patient visits, providers, provider groups, geographical areas, claims, and/or the like) may then be analyzed (e.g., in the multi-dimensional space) to determine similarities and/or differences between different subjects.

Figure 4A:
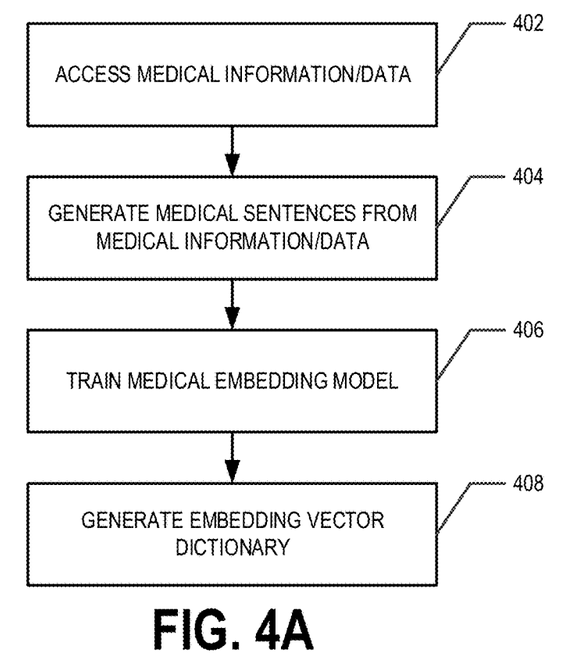
FIGS. 4A and 4B provide flowcharts illustrating example procedures, processes, and/or operations performed by a computing entity to generate and embedding vector dictionary and to provide aggregate vectors and/or a similarity metric for two or more subjects, in accordance with an example embodiment of the present invention.
Figure 4B:
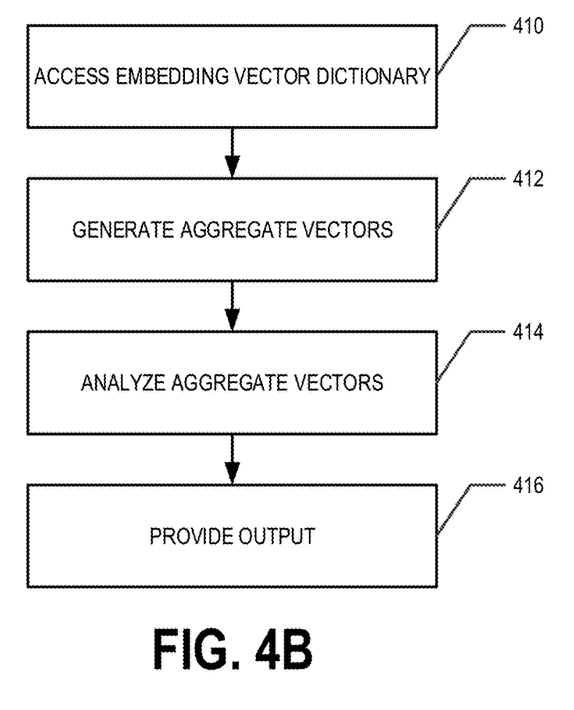

FIGS. 4A and 4B provide flowcharts illustrating processes, procedures, and/or operations for providing aggregate vectors and performing a similarity and/or difference analyses based thereon, according to an example embodiment. FIG. 4A illustrates generating an embedding vector dictionary. Starting at block 402, a plurality of instances of medical information/data is accessed. For example, the computing entity 200 may access a plurality of instances of medical information/data. In an example embodiment, the plurality of instances of medical information/data (or at least a portion thereof) are stored in a database or other data store by the computing entity 200. In an example embodiment, the plurality of instances of medical information/data (or at least a portion thereof) are accessed by providing a request for medical information/data to another computing entity 200 (e.g., via the communication interface 220) or data store and receiving the instances of medical information/data (e.g., via the communication interface 220) in response to the request. In an example embodiment, the request could identify a specific data range of medical information/data to be accessed. In an example embodiment, the medical information/data may be cleansed to remove patient names and/or other identifying information/data. For example, the generating of the embedding vector dictionary does not require patient identifiers or quasi-identifiers, thus protecting patient privacy.

In an example embodiment, an instance of medical information/data corresponds to a particular patient visit, a day in hospital, or collection of visits/days in a week/month or other time range. In an example embodiment, an instance of medical information/data may comprise a patient identifier; provider and/or provider group identifier(s); geographical information corresponding to the location of the particular visit (e.g., the street address, city, state, and/or the like where the particular patient visit occurred); demographic information/data corresponding to the patient; one or more medical codes corresponding to a diagnosis, procedure, prescription or drug, equipment and/or the like corresponding to the particular patient visit; a date of the particular patient visit; and/or the like. As noted above, the medical information/data may be cleansed to remove patient names and/or other identifying information/data. For example, the medical information/data may be cleansed such that only the medical codes and possibly a corresponding date and/or time is used in the construction of the plurality of medical sentences.

Figure 5:
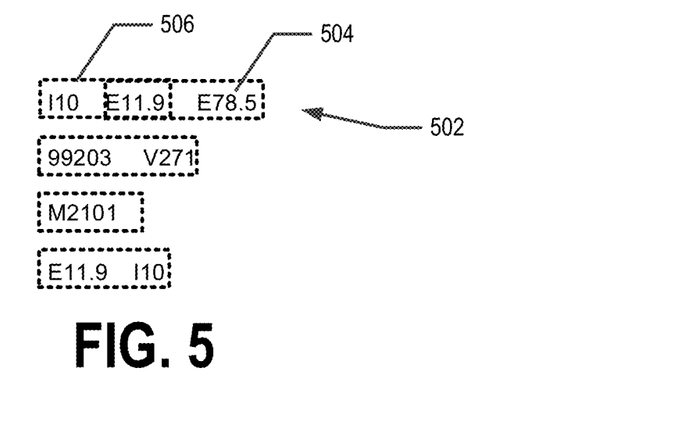
FIG. 5 illustrates an example set of one or more medical sentences, in accordance with an example embodiment of the present invention.

At block 404, a plurality of medical sentences are generated from the plurality of instances of medical information/data. For example, the computing entity 200 may generate a plurality of medical sentences from the plurality of instances of medical information/data. The plurality of instances may consist of all medical data from a payer, a government entity (VA, state Medicare claims); or a registry of patients with a specific disease or treatment. In an example embodiment, a medical sentence is a string of the medical codes (e.g., procedure codes, diagnosis codes, prescription or drug codes, equipment codes, revenue codes, place of service codes, and/or the like) corresponding to a particular time window. For example, the time window is one day, two days, a week, a month, a year, and/or the like. For example, if the time window is one day, a medical sentence may comprise each medical code and/or one or more medical codes from the instances of medical information/data corresponding to a particular patient identifier and the same date. In an example embodiment, a medical sentence consists of a string of one or more medical codes. In various scenarios, a medical sentence may be ten, twenty, or more medical codes long, but there is no bound to sentence length. For example, FIG. 5 provides an example list of medical sentences 502 each comprising one or more medical codes 504.

In various embodiments, the order of the medical codes within the medical sentence is randomized. For example, one or more medical codes may be extracted from an instance of medical information/data and then a medical sentence may be formed by generating a string of the one or more medical codes with the order of the one or more medical codes within medical sentence being randomized. In an example embodiment, two or more medical sentences may be generated from an instance of medical information/data. For example, two or more medical codes may be extracted from an instance of medical information/data, a first medical sentence may be formed by generating a string of the two or more medical codes, and then one or more additional medical sentences may be generated that are permutations of the first medical sentence. For example, the order of the two or more medical codes may be different in each of the first medical sentence and the two or more medical sentences. The randomization of medical codes within the medical sentences and/or the inclusion of permutations of medical sentences provides for a more robust determination of the relationships between various codes by the machine learning. Thus, the randomization of medical codes within the medical sentences and/or inclusion of permutations of medical sentences provides a medical embedding model that better captures the relationships between medical codes. Moreover, the randomization of medical codes within the medical sentences and/or inclusion of permutations of medical sentences aids the machine learning in overcoming the difficulties of generating vector embeddings for codes that do not follow a grammar.

In an example embodiment, the plurality of medical sentences may be filtered. For example, the plurality of medical codes may be filtered to only include medical sentences satisfying a minimum code length requirement. For example, the plurality of medical sentences may be filtered to only include medical sentences that comprise a minimum of two medical codes, a minimum of three medical codes, and/or the like. In an example embodiment, the set of medical sentences corresponding to a patient identifier (e.g., generated based on instances of medical information/data corresponding to the same patient/patient identifier) may be filtered to only include the first instance of each medical code. For example, if a patient is diagnosed with high cholesterol, multiple instances of medical information/data corresponding to the patient may comprise the diagnosis code for high cholesterol. The set of medical sentences corresponding to the patient may then be filtered to remove any repeated/duplicate diagnosis codes for high cholesterol. In another example embodiment, set of medical sentences corresponding to a patient identifier may be filtered to remove repeated/duplicate prescription/drug codes. For example, if a patient is prescribed a long term and/or maintenance drug (e.g., a statin) a plurality of instances of medical information/data may include the prescription/drug code corresponding to the long term and/or maintenance drug. The set of medical sentences corresponding to the patient may then be filtered to remove all but the first instance of the prescription/drug code. For example, if a patient gets a refill for her statin and picks up an antibiotic prescription for a sinus infection at the same time, an instance of medical information/data may include both the prescription/drug code corresponding to the statin and the prescription/drug code corresponding to the antibiotic. To prevent the medical embedding model from learning a false connection between the prescription/drug code corresponding to the statin and the prescription/drug code corresponding to the antibiotic, only the first instance of prescription/drug code corresponding to the statin may be included in the set of medical sentences corresponding to the patient/patient identifier. In various embodiments, this filtering may be executed between the steps of accessing the medical information/data and generating the medical sentences.

At block 406, the medical embedding model may be trained. For example, the computing entity 200 may train the medical embedding model using machine learning. For example, the one or more medical sentences may be used as a training data set to train the medical embedding model using machine learning. In an example embodiment, the medical embedding model is trained using unsupervised machine learning. In various embodiments, the medical embedding model may be a modified fastText, word2vec, GloVe, or other algorithm. For example, the medical embedding model may be an embedding layer of a deep net, neural network, and/or the like.

In an example embodiment, the medical embedding model is trained to transfer, link, associate, and/or the like a medical code to a multi-dimensional vector in a multi-dimensional space. In an example embodiment, the dimensionality of the multi-dimensional space may be predetermined, predefined, and/or configurable. In an example embodiment, the dimensionality of the multi-dimensional space may be determined based on user input. In an example embodiment, the dimensionality of the space may be determined based on an automatic determination and/or estimate of the number of dimensions required to fully encode the medical codes within the multi-dimensional space. In an example embodiment, the number of dimensions of the multi-dimensional space is in the inclusive range of 50 to 100 dimensions. In an example embodiment, the number of dimensions of the multi-dimensional space is in the inclusive range of 10 to 1000 dimensions. In various embodiments, the dimensions themselves do not have semantic meaning. Rather, the distances or angles between the multi-dimensional vectors within the multi-dimensional space provide semantic meaning to the model. For example, the medical embedding model may be trained using machine learning to assign, link, and/or associate a multi-dimensional vector to each of a plurality of medical codes based on the inter-relatedness of the medical codes such that the distance or angle between two multi-dimensional vectors within the multi-dimensional space indicates how closely and/or strongly related the two corresponding medical codes are.

In an example embodiment, the medical embedding model may be trained through the analysis of the one or more medical sentences using a code window. In various embodiments, the code window may be predetermined, predefined, or configurable. In an example embodiment, the code window is in the inclusive range of 2-10 codes. In a particular example, the code window may be predetermined to be 3 codes wide. In an example embodiment, the code window is a rolling code window. The medical embedding model may interpret codes that appear within the code window at the same time as being related. For example, FIG. 5 illustrates a set of four medical sentences 502 each comprising one or more medical codes 504. The medical sentences 502 may be analyzed using code windows 506 that are two codes wide, as shown by the dotted lines. Medical codes 504 that appear within the same code window 506 may be considered to be related. For example, medical codes I10 and E11.9 may be considered related, medical codes E11.9 and E78.5 may be considered related, and medical codes 99203 and V271 may be considered related. However, Codes I10 and V271 may not be considered related in this window, for example. In training the model, the number of times two medical codes appear within the same code window 506 throughout the analysis of the set of medical sentences, the stronger the relationship between the two medical codes is interpreted to be. For example, medical codes I10 and E11.9 may be considered more strongly related than medical codes 99203 and V271 or medical codes E11.9 and E78.5. Thus, the medical embedding model may link and/or associate the medical codes I10 and E11.9 to multi-dimensional vectors within the multi-dimensional space that are closer in distance and/or angle (within the multi-dimensional space) than the multi-dimensional vectors linked and/or associated to the medical codes 99203 and V271. For example, the multi-dimensional vectors linked and/or assigned to medical codes I10 and E11.9 may be separated by less distance or a smaller angle within the multi-dimensional space than the multi-dimensional vectors linked and/or assigned to medical codes E11.9 and E78.5.

Continuing with FIG. 4A, at block 408, an embedding vector dictionary is generated. For example, the computing entity 200 may use the medical embedding model to generate an embedding vector dictionary. The embedding vector dictionary may be stored in memory 210, 215. In an example embodiment, the embedding vector dictionary comprises a set of medical codes and the corresponding, linked, and/or assigned multi-dimensional vectors. For example, the embedding vector dictionary may indicate the multi-dimensional vector corresponding, linked, and/or assigned to each medical code of a plurality of medical codes. The multi-dimensional vectors assigned, linked, and/or corresponding to each of the medical codes may encode the relationships and/or strength of the relationships between pairs and/or groups of medical codes. In particular, the relative distance and/or angle within the multi-dimensional space between a first pair of multi-dimensional vectors corresponding to a first pair of medical codes and a second pair of multi-dimensional vectors corresponding to a second pair of medical codes may indicate the relative relatedness and/or strength of the relationships between the corresponding medical codes.

Figure 6:
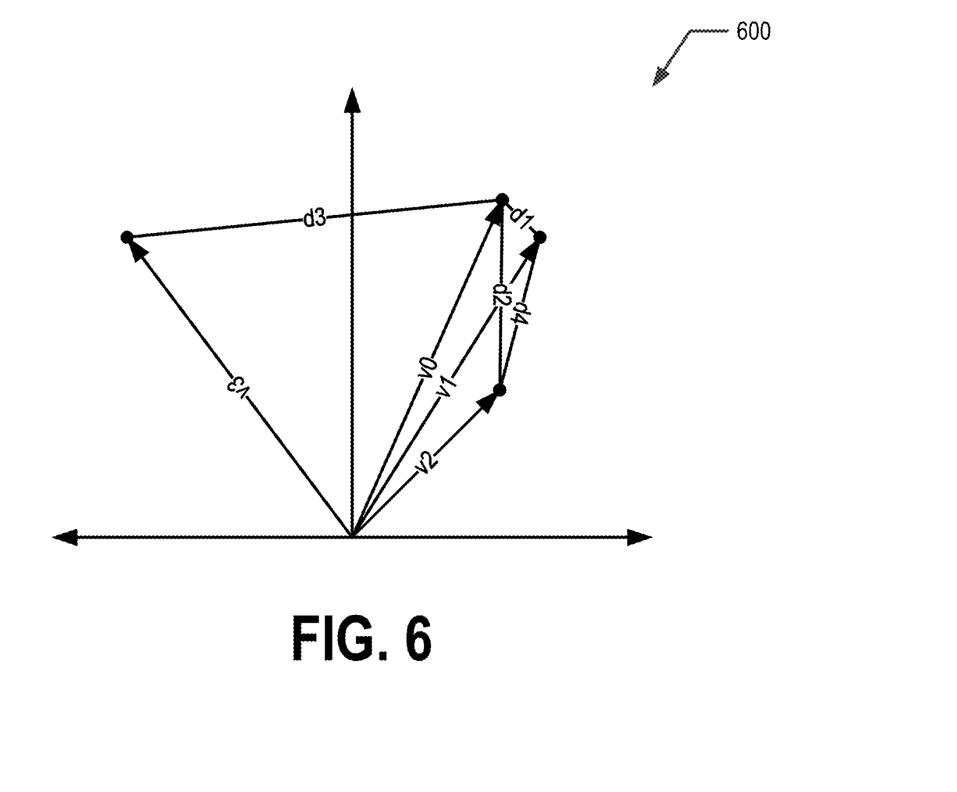
FIG. 6 illustrates a set of multi-dimensional vectors in a multi-dimensional space, in accordance with an example embodiment of the present invention.

For example FIG. 6 shows an illustrative example set of multi-dimensional vectors within multi-dimensional space 600 that were linked and/or assigned to medical codes I10, E11.9, E78.5, and V271 based on a medical embedding model trained using the set of medical sentences 502 and code window 506 shown in FIG. 5. For example $v_0$ corresponds to medical code I10, $v_1$ corresponds to medical code E11.9, $v_2$ corresponds to medical code E78.5, and $v_3$ corresponds to medical code V271. As can be seen in FIG. 6, $v_0$ and $v_1$ are separated by distance $d_1$, $v_0$ and $v_2$ are separated by distance $d_2$, $v_0$ and $v_3$ are separated by distance $d_3$, and $v_1$ and $v_2$ are separated by distance $d_4$. Distance $d_1$ is less than distances $d_2$ and $d_3$ indicating that medical code I10, corresponding to vector $v_0$, is more closely and/or strongly related to medical code E11.9, corresponding to vector $v_1$, than to medical codes E78.5 and V271, corresponding to vectors $v_2$ and $v_3$, respectively. Additionally, distance $d_2$ is less than distance $d_3$ indicating that medical code I10, corresponding to vector $v_0$, is more closely and/or strongly related to medical code E78.5, corresponding to vector $v_2$, than to medical code V271, corresponding to vector $v_3$. Moreover, distance $d_1$ is less than distance $d_4$, which in turn is less than distance $d_2$ indicating that medical codes I10 and E11.9, corresponding to vectors $v_0$ and $v_1$, respectively, are more closely and/or strongly related to each other than to medical code E78.5, corresponding to vector $v_2$ and that medical codes E11.9 and E78.5, corresponding to vectors $v_1$ and $v_2$, respectively, are more closely and/or strongly related to each other than to medical codes I10 and E78.5, corresponding to vectors $v_0$ and $v_2$, respectively. Furthermore, each of distances $d_1$, $d_4$, and $d_2$ are less than distance $d_3$, indicating that each of medical codes I10, E11.9, and E78.5 are more closely and/or strongly related to each other than to medical code V271, corresponding to vector $v_3$. In various embodiments, the distance within the multi-dimensional space may be Euclidean distance, cosine distance, and/or other distance measure within the multi-dimensional space. For example, in an example embodiment the distance between the multi-dimensional space is an angle or value indicative of an angle (e.g., cosine distance).

FIG. 4B provides a flowchart illustrating example processes, procedures, operations, and/or the like providing aggregate vectors based on an embedding vector dictionary, in accordance with an example embodiment. At block 410, an embedding vector dictionary may be accessed. For example, the computing entity 200 may access an embedding vector dictionary. In various embodiments, the embedding vector dictionary is generated as described above with respect to FIG. 4A and then stored in memory 210, 215. The embedding vector dictionary may then be accessed from the memory 210, 215 (e.g., by the processing element 205) such that the multi-dimensional vectors and the correspondence of the multi-dimensional vectors to medical codes may be used to generate one or more aggregate vectors for analysis.

At block 412, a plurality of aggregate vectors may be generated. For example, the multi-dimensional vectors assigned, linked, and/or corresponding to the medical codes of one or more instances of medical information/data may be aggregated to generate an aggregate vector. As described above, in an example embodiment, an instance of medical information/data corresponds to a particular patient visit, a day in hospital, or collection of visits/days in a week/month or other time range. In an example embodiment, an instance of medical information/data may comprise a patient identifier; provider and/or provider group identifier(s); geographical information corresponding to the location of the particular visit (e.g., the street address, city, state, and/or the like where the particular patient visit occurred); demographic information/data corresponding to the patient; one or more medical codes corresponding to a diagnosis, procedure, prescription or drug, equipment, treatment location, and/or the like corresponding to the particular patient visit; a date of the particular patient visit; and/or the like.

Figure 7:
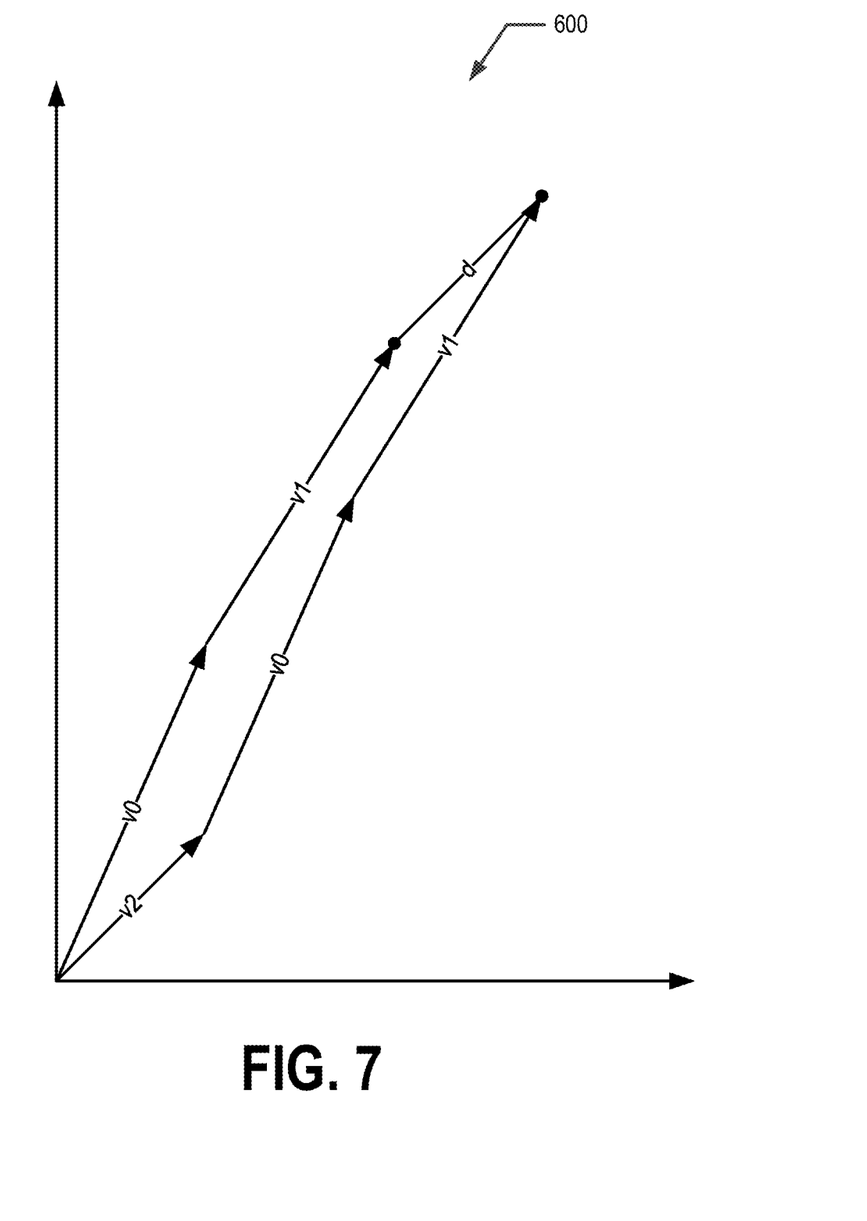
FIG. 7 illustrates two aggregate vectors in the multi-dimensional space, in accordance with an example embodiment of the present invention.

For example, the computing entity 200 may generate one or more aggregate vectors. For example, aggregate vectors may be generated using the embedding vector dictionary. For example, the correspondence, linking, and/or the like of multi-dimensional vectors to medical codes provided by the embedding vector dictionary may be used to generate the aggregate vectors. For example, FIG. 7 illustrates two aggregate vectors generated based on the instances of medical information/data corresponding to medical sentences I10 E11.9 E78.5 and E11.9 I10 in the multi-dimensional space 600. In the illustrated example, the multi-dimensional vectors corresponding to each of the medical codes of the medical sentence and/or corresponding instance of medical information/data are aggregated by adding the vectors together. In various embodiments, the multi-dimensional vectors corresponding to each of the medical codes of a medical sentence and/or corresponding instance of medical information/data may be aggregated by adding/summing the corresponding multi-dimensional vectors, averaging the corresponding multi-dimensional vectors, performing a weighted average of the corresponding multi-dimensional vectors, and/or performing another vector function on the corresponding multi-dimensional vectors to aggregate the corresponding multi-dimensional vectors to generate an aggregate vector corresponding to the medical sentence and/or instance of medical information/data. As shown in FIG. 7, the aggregate vectors corresponding to medical sentences I10 E11.9 E78.5 and E11.9 I10 are separated by a distance d, which provides a similarity metric indicating the similarity between the two medical sentences. In an example embodiment, the aggregate vectors may be normalized to a predefined length (e.g., unit length).

Further, an aggregate vector may be generated based on a subject. In various embodiments, a subject may be a patient, a particular patient visit, a provider, a provider group, a claim, and/or the like. For example, one or more instances of medical information/data corresponding to a patient (e.g., containing the patient identifier corresponding to the patient) may converted to an aggregate vector by aggregating the multi-dimensional vectors corresponding to the medical codes of the one or more instances of medical information/data, as indicated by the embedding vector dictionary. Similarly, the multi-dimensional vectors corresponding to medical codes of one or more instances of medical information/data having a same provider identifier, provider group identifier, claim identifier, and/or the like and/or corresponding to a particular patient visit may be aggregated to generate and/or form an aggregate vector corresponding to the provider, provider group, claim, and/or particular patient visit. As should be understood, aggregate vectors may be generated for a plurality of subjects. For example, an aggregate vector may be generated for each of a plurality of patients, providers, provider groups, claims, particular patient visits, and/or other subjects. The distances between pairs of the resulting vectors within the multi-dimensional space (e.g., Euclidean distance, cosine distance, angle, or other distance measure within the multi-dimensional space) provide a similarity metric between the corresponding pairs of subjects (e.g., patients, providers, provider groups, claims, particular patient visits, and/or the like).

At block 414 of FIG. 4B, the aggregate vectors may be analyzed. For example, the computing entity 200 may analyze the aggregate vectors. For example, the computing entity 200 may identify a predetermined, predefined, and/or configurable number of one or more closest aggregate vectors, which are the predetermined, predefined, and/or configurable number of aggregate vectors that have the smallest distances to an investigation aggregate vector. For example, the computing entity 200 may identify all of the aggregate vectors that satisfy a threshold distance requirement with respect to an investigation aggregate vector. For example, the computing entity 200 may identify a predetermined, predefined, and/or configurable number of one or more furthest aggregate vectors, which are the predetermined, predefined, and/or configurable number of aggregate vectors that have the largest distances to an investigation aggregate vector. The aggregate vectors closest to and/or having the smallest distance to the investigation aggregate vector correspond to subjects that are most similar to the investigation subject corresponding to the investigation aggregate vector. The aggregate vectors furthest from and/or having the largest distance to the investigation aggregate vector correspond to subjects that are least similar to and/or the most different from the investigation subject corresponding to the investigation aggregate vector.

At block 416, an output is provided. For example, the computing entity 200 may provide an output identifying the investigation subject, the investigation aggregate vector, one or more identified similar or different aggregate vectors, one or more similar or different subjects corresponding to the one or more identified similar or different aggregate vectors, a distance measure between the investigation aggregate vector and one or more other aggregate vectors, and/or the like. In an example embodiment, the computing entity 200 may provide the output via an output device of the computing entity 200 (e.g., a display device, a user interface, an audio output, cause a printer to print the output, and/or the like). In an example embodiment, the output is provided as input to another application and/or program operating on the computing entity 200. In an example embodiment, the computing entity 200 may provide (e.g., transmit) the output via a network interface 220. For example, the user computing entity 30 may receive the output (e.g., via network interface 320 or receiver 306) and cause display of at least a portion of the output via display 316, and/or the like.

As noted above, this output may be used to identify subjects from a population of subjects that are most similar or most different/least similar to an investigation subject. In various embodiments, subjects may be patients, particular patient visits, providers, provider groups, geographical areas, health insurance claims, and/or the like. For example, various embodiments of the present invention may be used to identify one or more provider groups that are most like an investigation provider group by generating aggregate vectors based on medical codes extracted from instances of medical information/data corresponding to the provider groups and the embedding vector dictionary. The provider groups that correspond to the aggregate vectors that are the least distance and/or within a first distance threshold of the investigation aggregate vector corresponding to the investigation provider group are the provider groups of the population of considered provider groups that are most similar to the investigation provider group. Similarly, subjects that are different from an investigation subject may be identified by identifying aggregate vectors that are a large distance or greater than a second distance threshold from an investigation aggregate vector corresponding to the investigation subject. In an example embodiment, a similarity/difference analysis may be performed for a group of subjects without the use of an investigation subject by identifying clusters of aggregate vectors corresponding to particular subjects of the group of subjects and/or identifying aggregate vectors that are a larger than a second distance threshold from one another. The output may comprise a list of identified similar or different subjects and the investigation subject, in an example embodiment.

Various embodiments may be used for linking related insurance claims. For example, if an original insurance claim is denied, the claim may be modified and resubmitted as another insurance claim. The resubmitted insurance claim generally does not identify the original claim. So for example, to identify the resubmitted claim as being a resubmitted claim and to identify and link the original claim to the resubmitted claim, a pool of one or more second claims may be identified. For example, the pool of second claims may comprise and/or consist of all claims with the same member ID, provider ID, and date of service. Aggregate vectors may then be generated corresponding to each of the second claims. In an example embodiment, an aggregate vector is generated from a claim by aggregating multi-dimensional vectors for each of the medical codes present in the claim. The second claim that corresponds to an aggregate vector with the smallest distance to the investigation aggregate vector corresponding to the investigation claim is likely the original claim if the investigation claim is a resubmitted claim. In an example embodiment, if an aggregate vector corresponding to a second claim is within a first threshold distance of the investigation aggregate vector corresponding to the investigation claim, then the investigation claim is likely a resubmitted claim and the identified second claim is likely the corresponding original claim. In various embodiments, the first threshold distance may be defined via empirical analysis, statistical analysis, machine learning, and/or the like. For example, the output may provide an indication that no second claim was identified (e.g., the investigation claim may be an original claim and not a resubmitted claim), a linking of the investigation claim to the identified second claim, identifiers for the investigation claim and identified second claim pair, and/or the like.

In another example, various embodiments may be configured to train (e.g., via machine learning) and/or use predictive models that are based on aggregate vectors corresponding to subjects. For example, a predictive model may be used to predict the occurrence of a clinical event for an investigation subject based on the corresponding investigation aggregate vector. For example, the predictive model may be trained using machine learning with a training data set comprising a plurality of aggregate vectors. For example, aggregate vectors for a population of patients may be generated and used as a training data set. After the predictive model is trained, an investigation aggregate vector may be provided and the predictive model may provide a likelihood that the investigation subject (e.g., a particular patient) will experience one or more clinical events. In an example embodiment, the likelihood that the investigation subject will experience the one or more clinical events corresponds to a predetermined, predefined, configurable, or other time period. In an example embodiment, the likelihood of a clinical event may be the probability that a particular medical code, set of medical codes, one of a set of medical codes, medical code and/or set thereof corresponding to an aggregate vector that is within a predefined distance of a prediction vector, and/or the like.

As should be understood, various embodiments provide an improvement over current automated medical information/data analysis. For example, current methods of automated medical information/data analysis include binary encoding an instance of medical information/data that results in each instance of medical information/data having a dimensionality equal to the dimensionality of the set of medical codes. For example, the current procedural terminology (CPT) codes alone define 10,000 codes and ICD-10 diagnoses define over 70,000 codes. Thus, these binary encodings are of very high dimensionality and fail to capture the similarity between two instances of medical information/data. For example, the diagnosis code for a left arm fracture is different from the diagnosis code for an identical right arm fracture. The binary encodings for a patient with a left arm fracture and another patient with an identical right arm fracture would fail to show the similarity between the two patients' clinical events. Thus, the current automated medical information/data analysis fails to be able to provide models that are efficient in terms of computing and memory resources and that can harness the insight of medical domain knowledge (e.g., that a left arm fracture and an identical right arm fracture are similar medical events). The separation of codes into procedure and diagnosis sets also means that one cannot easily determine that the broken arm is associated with certain radiology, surgery and immobilization procedures. The association among these codes is only possible through advanced methods like these code embeddings.

Moreover, automated generation of vector embeddings corresponding to medical codes is more complicated than automated generation of vector embeddings corresponding to words or textual information. In particular, the techniques used for natural language processing fail for processing medical codes as medical codes do not follow a particular grammar. Thus, embodiments of the present invention provide an improvement to computer technology and the technical field of automated processing of medical information/data represented as medical codes. For example, the random order of the medical codes in the medical sentences and/or the use of multiple permutations of a medical sentence in the training data set and/or the filtering of sentences corresponding to a patient identifier to only include the first instance of a prescription code help prevent the training of false relationships between codes and provides a more robust and insightful vector embedding. Thus, embodiments of the present invention provide an improvement to computer technology by providing a technique for expanding the use of embeddings from textual information to general information that does not follow a grammar.

V. Conclusion

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for providing aggregate vectors in a multi-dimensional space, the method comprising:
    accessing, by a computing entity comprising a processor and a memory storing computer program code, a plurality of instances of medical information encoded using medical codes;
    generating, by the computing entity, a plurality of medical sentences based at least in part on the plurality of instances of medical information, wherein (a) each medical sentence comprises one or more medical codes, (b) at least two medical sentences of the plurality of medical sentences are generated from the same instance of medical information of the plurality of instances of medical information, and (c) the at least two medical sentences are different from one another;
    generating, by the computing entity, an embedding vector dictionary comprising a plurality of multi-dimensional vectors (a) based at least in part on a medical embedding model trained using machine learning and the plurality of medical sentences, and (b) in a multi-dimensional space having a configurable dimensionality, each multi-dimensional vector corresponding to a medical code;
    generating, by the computing entity, a plurality of aggregate vectors based at least in part on the embedding vector dictionary;
    analyzing, by the computing entity, at least a portion of the plurality of aggregate vectors to identify two or more aggregate vectors that are similar or different based at least in part on a distance or angle between the two or more aggregate vectors in the multi-dimensional space; and
    providing, by the computing entity, an output comprising the identified two or more aggregate vectors.

2. The method of claim 1, wherein the dimensionality of the multi-dimensional space is in the range of 10-1000 dimensions.

3. The method of claim 1, further comprising randomizing the order of the medical codes within at least one of the plurality of medical sentences before training the medical embedding model using machine learning and the plurality of medical sentences.

4. The method of claim 1, further comprising, for at least one medical sentence of the plurality of medical sentences, generating a plurality of unique medical sentences by randomly reordering one or more medical codes within the medical sentence.

5. The method of claim 1, wherein at least one instance of medical information is filtered to remove a repeated medical code before the generation of the plurality of medical sentences.

6. The method of claim 1, wherein the machine learning uses a predetermined code window.

7. The method of claim 6, wherein the predetermined code window is in the range of 2-10 codes.

8. The method of claim 1, wherein (a) the plurality of aggregate vectors comprise a first claim vector and a plurality of second claim vectors, and (b) analyzing the at least a portion of the plurality of aggregate vectors comprises identifying one or more second claim vectors of the plurality of second claim vectors that is most similar to the first claim vector.

9. The method of claim 8, wherein at least one of the one or more second claim vectors has the smallest distance to the first claim vector of the plurality of second claim vectors in the multi-dimensional space.

10. The method of claim 1, wherein (a) the plurality of aggregate vectors comprises a first vector and a plurality of second vectors, (b) the first vector is one of (i) a patient vector, (ii) a provider vector, (iii) a provider group vector, or (iv) a geographical vector, and (c) analyzing the at least a portion of the aggregate vectors comprises identifying one or more second vectors that are similar to or different from the first vector based at least in part on distances between the first vector and each of the one or more second vectors in the multi-dimensional space.

11. The method of claim 1, wherein analyzing the at least a portion of the plurality of aggregate vectors comprises determining a clinical event prediction, wherein determining the clinical event prediction comprises:
    analyzing an investigation subject with a predictive model trained using machine learning using a training data set comprising at least a portion of the plurality of aggregate vectors.

12. An apparatus comprising at least one processor and at least one memory including computer program code for one or more programs, the at least one memory and the computer program code configured to, with the at least one processor, cause the apparatus to perform at least the following:
    access a plurality of instances of medical information encoded using medical codes;
    generate a plurality of medical sentences based at least in part on the plurality of instances of medical information, wherein (a) each medical sentence comprises one or more medical codes, (b) at least two medical sentences of the plurality of medical sentences are generated from the same instance of medical information of the plurality of instances of medical information, and (c) the at least two medical sentences are different from one another;
    generate an embedding vector dictionary comprising a plurality of multi-dimensional vectors (a) based at least in part on a medical embedding model trained using machine learning and the plurality of medical sentences, and (b) in a multi-dimensional space having a configurable dimensionality, each multi-dimensional vector corresponding to a medical code;
    generate a plurality of aggregate vectors based at least in part on the embedding vector dictionary;
    analyze at least a portion of the plurality of aggregate vectors to identify two or more aggregate vectors that are similar or different based at least in part on a distance between the two or more aggregate vectors in the multi-dimensional space; and
    provide an output comprising the identified two or more aggregate vectors.

13. The apparatus according to claim 12, wherein the at least one memory including computer program code for the one or more programs is further configured to, with the at least one processor, cause the apparatus to randomize the order of the medical codes within at least one of the plurality of medical sentences before training the medical embedding model using machine learning and the plurality of medical sentences.

14. The apparatus according to claim 12, wherein the at least one memory including computer program code for the one or more programs is further configured to, with the at least one processor, cause the apparatus to, for at least one medical sentence of the plurality of medical sentences, generate a plurality of unique medical sentences by randomly reordering one or more medical codes within the medical sentence.

15. The apparatus according to claim 12, wherein the machine learning uses a predetermined code window.

16. The apparatus according to claim 12, wherein (a) the plurality of aggregate vectors comprise a first claim vector and a plurality of second claim vectors, and (b) analyzing the at least a portion of the plurality of aggregate vectors comprises identifying one or more second claim vectors of the plurality of second claim vectors that is most similar to the first claim vector.

17. The apparatus according to claim 16, wherein at least one of the one or more second claim vectors has the smallest distance to the first claim vector of the plurality of second claim vectors in the multi-dimensional space.

18. The apparatus according to claim 12, wherein (a) the plurality of aggregate vectors comprises a first vector and a plurality of second vectors, (b) the first vector is one of (i) a patient vector, (ii) a provider vector, (iii) a provider group vector, or (iv) a geographical vector, and (c) analyzing the at least a portion of the aggregate vectors comprises identifying one or more second vectors that are similar to or different from the first vector based at least in part on distances between the first vector and each of the one or more second vectors in the multi-dimensional space.

19. The apparatus according to claim 18, wherein analyzing the at least a portion of the plurality of aggregate vectors comprises determining a medical event prediction, wherein determining the medical event prediction comprises:

training a medical event network using a machine learning algorithm using a training data set comprising at least a portion of the plurality of aggregate vectors, and analyzing the first vector using the medical event network.

20. A computer program product comprising at least one non-transitory computer-readable storage medium having computer-executable program code portions stored therein, the computer-executable program code portions comprising program code instructions, the computer program code instructions, when executed by a processor of a computing entity, are configured to cause the computing entity to at least:
access a plurality of instances of medical information encoded using medical codes;
generate a plurality of medical sentences based at least in part on the plurality of instances of medical information, wherein (a) each medical sentence comprises one or more medical codes, (b) at least two medical sentences of the plurality of medical sentences are generated from the same instance of medical information of the plurality of instances of medical information, and (c) the at least two medical sentences are different from one another;
generate an embedding vector dictionary comprising a plurality of multi-dimensional vectors (a) based at least in part on a medical embedding model trained using machine learning and the plurality of more medical sentences, and (b) in a multi-dimensional space having a configurable dimensionality, each multi-dimensional vector corresponding to a medical code;
generate a plurality of aggregate vectors based at least in part on the embedding vector dictionary;
analyze at least a portion of the plurality of aggregate vectors to identify two or more aggregate vectors that are similar or different based at least in part on a distance between the two or more aggregate vectors in the multi-dimensional space; and
provide an output comprising the identified two or more aggregate vectors.

* * * * *